United States Patent [19]
Krausman et al.

[11] Patent Number: 6,095,991
[45] Date of Patent: Aug. 1, 2000

[54] AMBULATORY BODY POSITION MONITOR

[75] Inventors: David T. Krausman, Kingsville; Richard P. Allen, Arnold, both of Md.

[73] Assignee: Individual Monitoring Systems, Inc., Baltimore, Md.

[21] Appl. No.: 09/121,394

[22] Filed: Jul. 23, 1998

[51] Int. Cl.[7] .................................................. A61B 5/103
[52] U.S. Cl. ........................................................ 600/595
[58] Field of Search ..................................... 600/587, 595

[56] References Cited

U.S. PATENT DOCUMENTS

| | | | |
|---|---|---|---|
| 4,348,562 | 9/1982 | Florin | 200/52 R |
| 4,846,195 | 7/1989 | Alt | 600/595 |
| 5,146,206 | 9/1992 | Callaway | 340/573 |
| 5,197,489 | 3/1993 | Conlan | 128/782 |
| 5,375,610 | 12/1994 | LaCourse et al. | 182/782 |
| 5,513,651 | 5/1996 | Cusimano et al. | 128/782 |
| 5,523,742 | 6/1996 | Simkins et al. | 340/573 |
| 5,533,520 | 7/1996 | Inguaggiato | 128/782 |
| 5,573,013 | 11/1996 | Conlan | 128/782 |
| 5,610,590 | 3/1997 | Johnson et al. | 340/573 |
| 5,749,372 | 5/1998 | Allen et al. | 128/782 |

*Primary Examiner*—Eric F. Winakur
*Assistant Examiner*—Pamela Wingood
*Attorney, Agent, or Firm*—Larry J. Guffey

[57] ABSTRACT

The present invention provides apparatus and methods for monitoring and recording the position and extent of motion of the body of a human or a lower animal. In a preferred embodiment of the invention, it comprises: (1) a three-dimensional-position monitoring, mercury sensor, (2) a programmable control unit that receives as input the output from the sensor and has the capability to sufficiently interpret said input so as to determine the position and related movements with respect to gravity of the measurement site at which said sensor is located on its user's body, (3) a storage device, operable by said control unit, that stores time-stamped, data regarding the user's body position and related movements, and (4) an interface device that has the capability of transferring the stored data to an external computer. The present invention for ambulatory recording eliminates the requirement that such monitors be connected through cables to external data storage and processing devices, thereby often effectively dictating that such monitoring activities be conducted in clinical laboratories.

9 Claims, 10 Drawing Sheets

AMBULATORY BODY POSITION MONITOR

BACKGROUND OF THE INVENTION

1. Field of the Invention

The present invention generally relates to an ambulatory apparatus and methods for monitoring and recording the position of the body and the extent of motion in each position of the body of a human or a lower animal.

2. Description of the Related Art

A human or lower animal can engage in a wide range of body movements. The observation of such body positions and movements can provide much valuable information to medical practitioners and researchers.

Direct visual observations of body positions and related movements in each position are labor intensive, time consuming and tedious. Moreover, direct visual observations provide only a limited range of qualitative information, which is itself subject to question as such observations themselves may cause the subject to become conscious of and thereby alter his or her movements.

Activity monitors have been developed for observing and quantifying certain aspects of bodily motions. However, existing monitors do not allow for the identification and recording of basic body positions or the level of movement activity being experienced while the body is in such basic positions. For example: (1) the invention of Johnson et al. (U.S. Pat. No. 5,610,590) measures only body motion during sleep, (2) Colon's invention (U.S. Pat. No. 5,573,013) measures activity of the wrist, (3) the invention of Simkins et al. (U.S. Pat. No. 5,523,742) generates voltage signals during epilepsy seizures, (4) the integrated movement analyzing system of Cusimano et al. (U.S. Pat. No. 5,513,651) uses body electrodes tethered to recording apparatus to measure muscle activity, (5) LaCourse et al. (U.S. Pat. No. 5,375,610) use mercury switches contained in a body suit to measure activity, (6) Callaway's invention (U.S. Pat. No. 5,146,206) detects body movement when a patient is alighting from bed preparatory to ambulation, and (7) an activity monitor using a single mercury tilt switch developed by Florin (U.S. Pat. No. 4,348,562) attaches to an alarm to signal a patient's body position change from the supine position. None of this related art is seen to provide for ambulatory, non-tethered identification and recording of various basic body positions or the level of movement activity being experienced while the body is in such basic body positions. Knowledge of this level of movement activity makes it possible to distinguish between various forms of bodily activities that might be performed in the same basic body position; for example, to distinguish walking from merely standing upright.

An apparatus or method for monitoring and recording the basic positions of the body and the extent of motion of a body in each such positions could overcome the above noted disadvantages of prior monitors, and would be a valuable tool in many areas of medicine, including: (1) research, diagnosis and treatment of sleep disorders and neurological abnormalities (e.g., epilepsy and hyperactivity), (2) for reducing the risk of sudden infant death syndrome (SIDS), where it has been shown that babies sleeping in the prone position are more likely associated with an increased risk of crib deaths, (3) osteoporosis research, where the effects of weight bearing are studied on bone development and atrophy, (4) for the bedridden, to reduce the risk of bed sores, (5) treatment of various medical conditions, such as post-surgical recovery or certain forms of arthritis, where maintaining a minimum amount of time standing or sitting is considered an important part of the treatment, and (6) in addition to human applications, for the study of the effects of medications and the environment on the positional activity and behavior of lower animals.

For example, for sleep disorders such as sleepwalking, diagnosis and treatment evaluation has been hampered by the problems associated with recording relatively rare events which are not typically remembered by the patient. Thus, the number, time of occurrence and pattern of motor behavior for the typical patient's sleepwalking events has therefore never been adequately monitored and recorded. Doing so would require at least minute by minute recording of the patient's body positions over many days while the patient stays in the comfort and convenience of their own home.

Recognizing the need for an improved apparatus or method for monitoring and recording body positions and the extent of motion in each such position, it is therefore a general object of the present invention to provide a novel ambulatory, body position monitor having additional recording and alarm-sounding capabilities.

SUMMARY OF THE INVENTION

The present invention is generally directed to satisfying the needs set forth above and the problems identified with prior body monitors. The problems, of having to harness the to-be-monitored subject to laboratory recording equipment and the monitor's insufficient responsive capabilities to the data being collected, are resolved by the present invention.

In accordance with one preferred embodiment of the present invention, the foregoing need can be satisfied by providing an ambulatory body position monitor comprising:

a three-dimensional-position monitoring, mercury sensor, a programmable control unit that receives as input some form of the output from said sensor, said control unit having the capability to sufficiently interpret said input so as to determine the position and related movements with respect to gravity of the measurement site at which said sensor is located on its user's body, a storage device, operable by said control unit, that stores time-stamped, data regarding the user's body position and related movements, and an interface device, operable by said control unit, that has the capability of transferring said stored data to an external computer, a display unit, operable by said control unit, that visually communicates information regarding the user's body position, wherein, for monitoring subjects with sleepwalking and other sleep disorders and for which it is necessary to distinguish between the user's positions of sitting, walking or standing, a first monitor is situated on the user's chest and a second monitor is situated at a location chosen from among the group consisting of locations on the thigh and the ankle;

where it is understood that the description above is meant to generally illustrate the present invention, and not in any way limit the many embodiments in which it can be practiced. For example, it is clear that this invention could also take the form of a method for monitoring body position.

This new ambulatory body position monitor is seen to achieve its primary object of providing an improved position monitor having additional recording and alarm-sounding capabilities. Furthermore, this monitor eliminates the requirement that such monitors be connected through cables to external data storage and processing devices, thereby often effectively dictating that such monitoring activities be conducted in clinical laboratories.

Another object of the current invention is to provide an apparatus and method for monitoring and recording the position and extent of motion of a body that will be a valuable tool in many areas of medicine, including: (1) treatment of those with sleep disorders and neurological abnormalities, (2) for reducing the risk of sudden infant death syndrome (SIDS), (3) osteoporosis research, (4) for the bedridden, to reduce the risk of bed sores, (5) treatment of various medical conditions, such as post-surgical recovery or certain forms of arthritis, and (6) in addition to human applications, for the study of the effects of medications and the environment on the positional activity and behavior of lower animals.

Other objects and advantages of this invention will become readily apparent as the invention is better understood by reference to the accompanying drawings and the detailed description that follows.

DESCRIPTION OF THE PREFERRED EMBODIMENT

Figure 1:
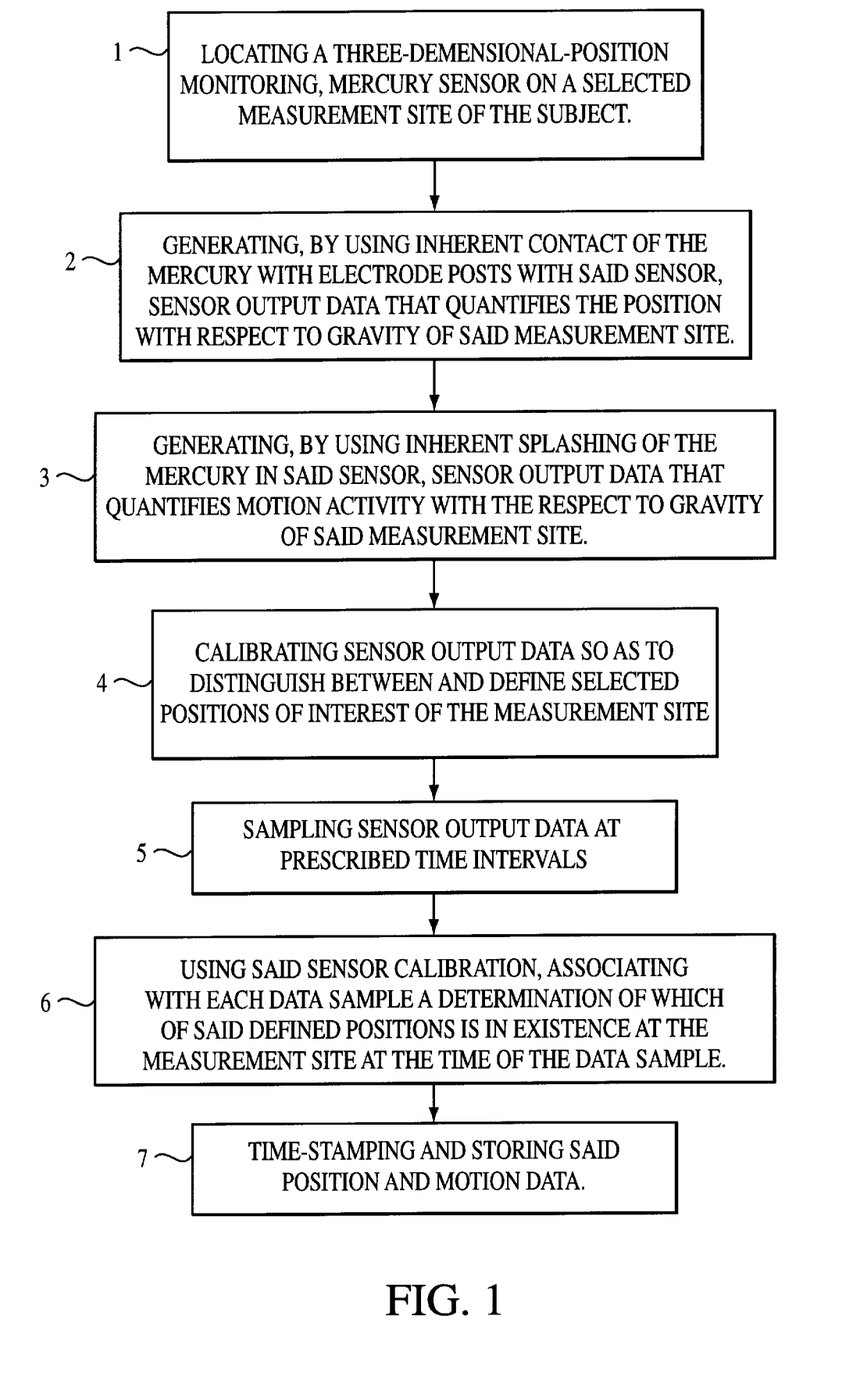
FIG. 1 is a schematic flow diagram which depicts a method in accordance with a preferred embodiment of the present invention.

Referring now to the drawings wherein are shown preferred embodiments and wherein like reference numerals designate like elements throughout, there is shown in FIG. 1 a schematic flow diagram which depicts a method in accordance with a preferred embodiment of the present invention for monitoring and recording the position of the body of a fully ambulatory subject.

In this embodiment the method is seen to comprise the steps of (1) locating a three-dimensional-position monitoring, mercury sensor on a selected measurement site of the subject, (2) generating, by using inherent contact of the mercury with various electrode posts within said sensor, sensor output data that quantifies the position with respect to gravity of said measurement site, (3) generating, by using inherent splashing of the mercury in said sensor, sensor output data that quantifies motion activity with respect to gravity of said measurement site, (4) calibrating sensor output data so as to distinguish between and define selected positions of interest of the measurement site, (5) sampling sensor output data at prescribed time intervals, (6) using said sensor calibration, associating with each data sample a determination of which of said defined positions is in existence at the measurement site at the time of the data sample, and (7) time-stamping and storing said position data.

Figure 2:
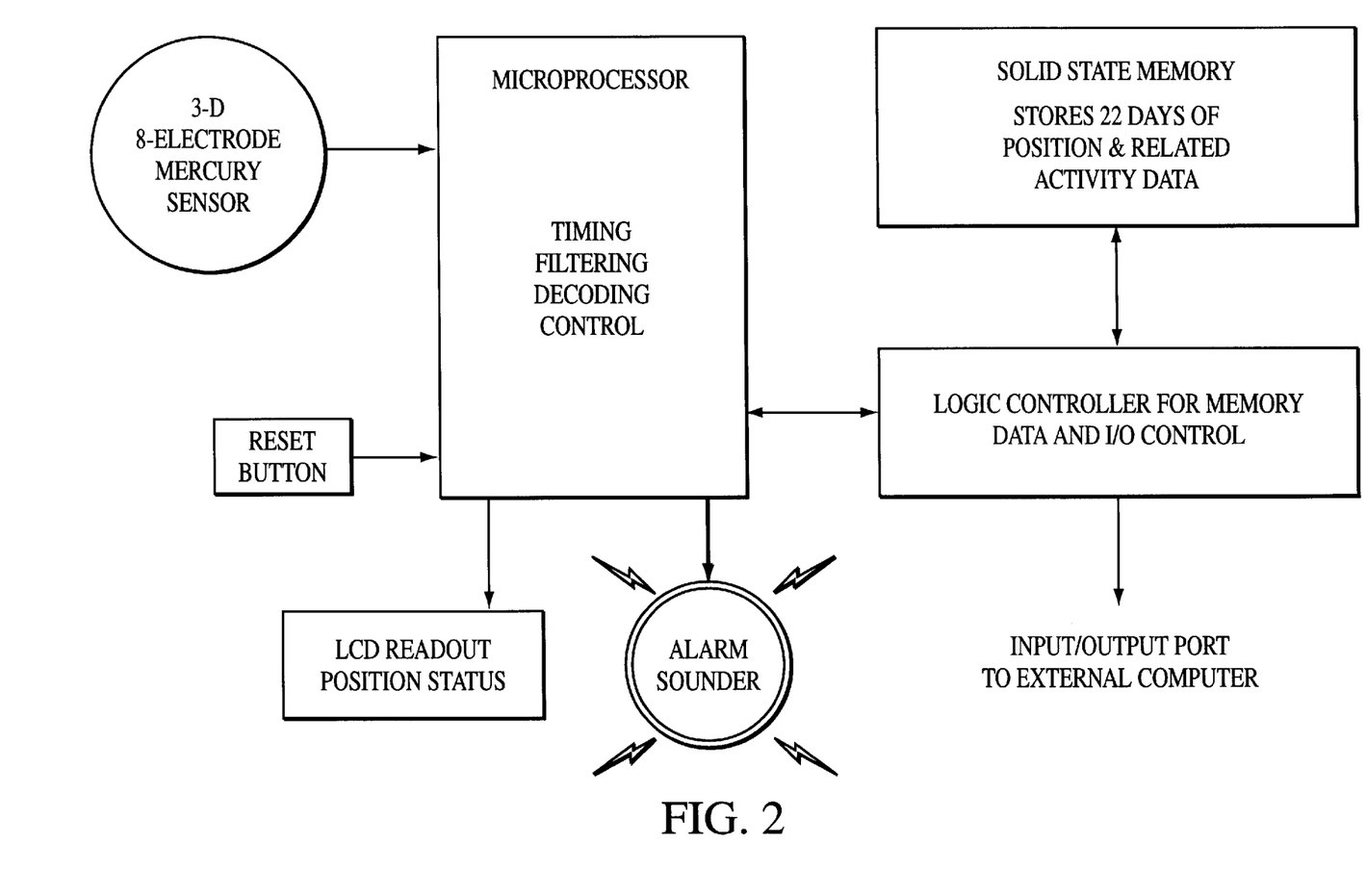
FIG. 2 is a front view of a suitable mercury sensor for the practice of the embodiment of the invention shown in FIG. 1.

In another preferred embodiment, the present invention is seen to take the form of an ambulatory body position monitor. A general overview of this embodiment is shown in FIG. 2 which provides a schematic block diagram of an ambulatory body position monitor. It comprises: (1) a three-dimensional-position monitoring, mercury sensor, (2) a programmable control unit that receives as input the output from the sensor and has the capability to sufficiently interpret said input so as to determine the position and extent of motion with respect to gravity of the measurement site at which said sensor is located on its user's body, (3) a storage device, operable by said control unit, that stores time-stamped, data regarding both the user's body position and the motion activity relative to the body position, and (4) an interface device that has the capability of transferring the stored data to an external computer.

Figure 3A:
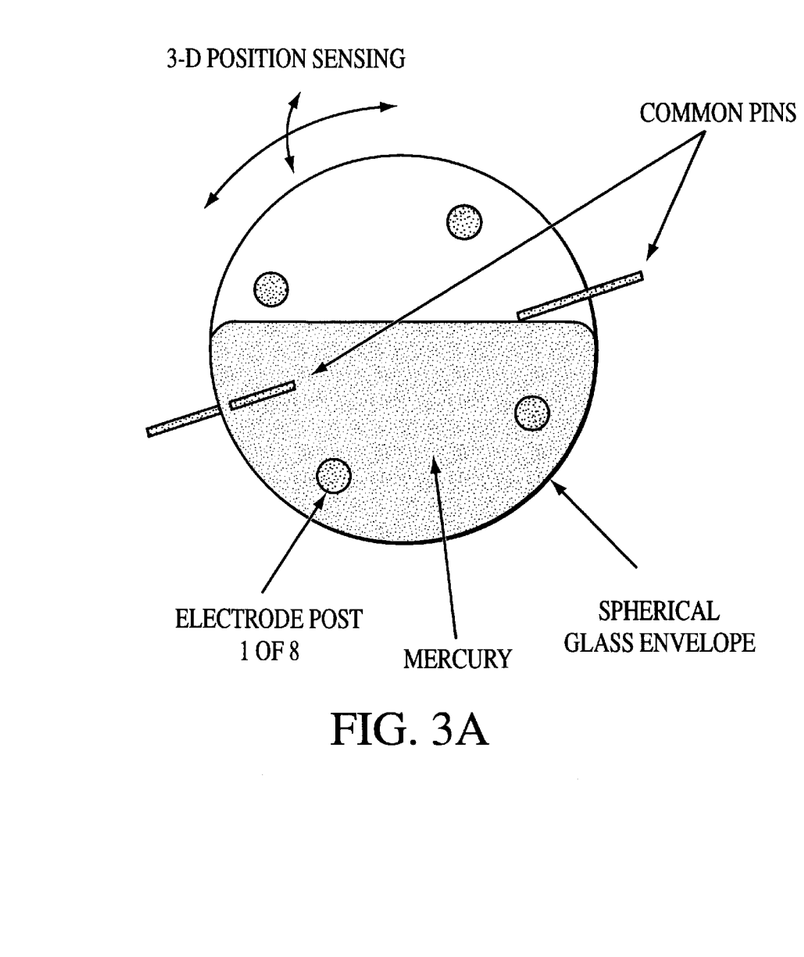
FIG. 3 is a schematic block diagram which depicts an ambulatory body position monitor in accordance with a preferred embodiment of the present invention.
Figure 3B:
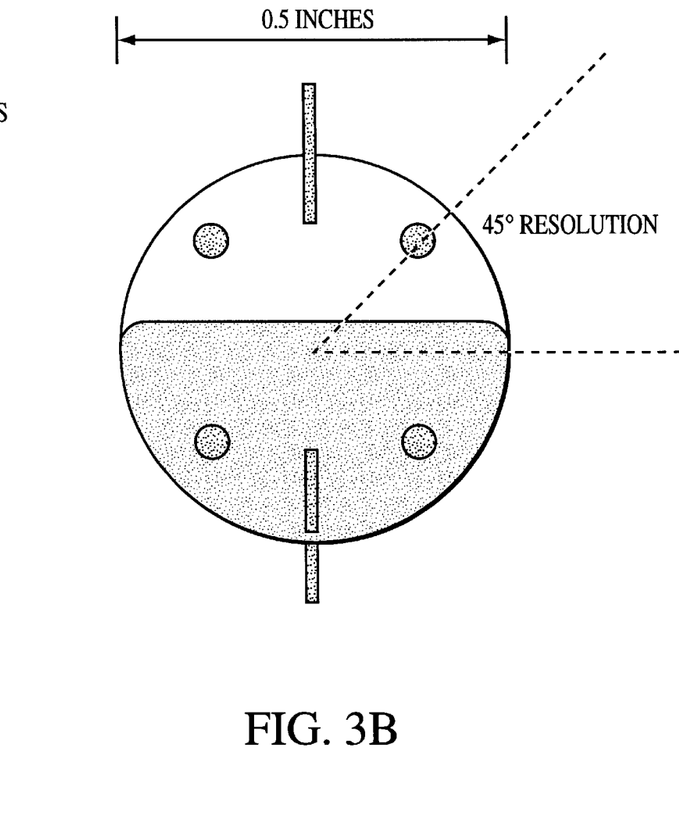

A suitable mercury sensor for the practice of the embodiments of the invention shown in FIGS. 1 and 2 has been found to be a modified version of the miniaturized Sandia Switch manufactured by Fifth Dimension, Inc., Trenton, N.J., and originally developed for Sandia Laboratories and military applications. This sensor is shown in FIG. 3 to consist of a globular shaped, glass envelope that measures approximately 1.3 cm in diameter and contains sixteen electrode posts, eight of which are used as active elements and eight of which are used as reference elements. These are equally spaced around the surface of the envelope to accurately register the physical position of the envelope relative to gravity.

Within this envelope, a small pool of mercury covers the bottom-most group of electrode posts. From experimentation for the development of a monitor for use in the study of patients with sleepwalking and other sleep disorders, it was found that the best results were achieved by using a mercury pool of approximately 1000 mg. As the sensor envelope is rotated, the mercury covered electrode groupings change and yield sensor outputs through the contacts. The information from the eight active elements gives 256 unique outcome values which are each matched with a truth table to determine the sensor's current position relative to gravity.

The output from this sensor with appropriate software detection and digital filter algorithms was found to be such as to allow one to distinguish and define forty basic body positions of interest. For the monitoring of patients with sleep disorders, it was found sufficient to utilize only six (ie., patient lying supine, prone, or on right or left side, sitting, walking) of these forty positions to characterize the patient's body position and motion during periods of sleep.

This sensor-positional-resolution capability was achieved by wiring each of the sensor's active electrode posts to the parallel input port of a computer. Eight-bit binary data values were then generated and stored as a reference truth table to establish a database of information identifying each rotational position of the sensor as the sensor was rotated in three dimensions. Additionally, for visual verification, the eight active electrode posts were connected through a battery to eight individual LED lights. The sensor was then rotated while noting which combinations of LEDs would light indicating which electrodes were contacting the pool of mercury residing at the bottom of the envelope. Each physical position relative to gravity presented a different pattern of lights. Shaking the envelope produced an effect in which all the LEDs would flash or sparkle, with the group of LEDs representing the dominate physical position glowing the brightest. Thus, no matter how much mercury splashing might be generated by walking or other motions, a software filter could easily distinguish the envelope's physical position.

For a programmable control unit suitable for use in this embodiment, a microprocessor is used to provide signal filtering, timing, control and position decoding capabilities. A suitable microprocessor has been found to be the ultra-low power CMOS micro controller Microchip PIC16C74, operating at 32,768 hertz with a 4K×14 bit internal, nonvolatile resident memory for the microprocessor's application program, with an on-chip 8 channel, 8 bit analog to digital converter, 33 input/output pins and a serial communications interface (SCI). The eight active elements of the sensor are directly interfaced to the 8 bit input port of the microprocessor. Support components and circuit chips were of surface mount technology (SMT).

Figures 8, 8A:
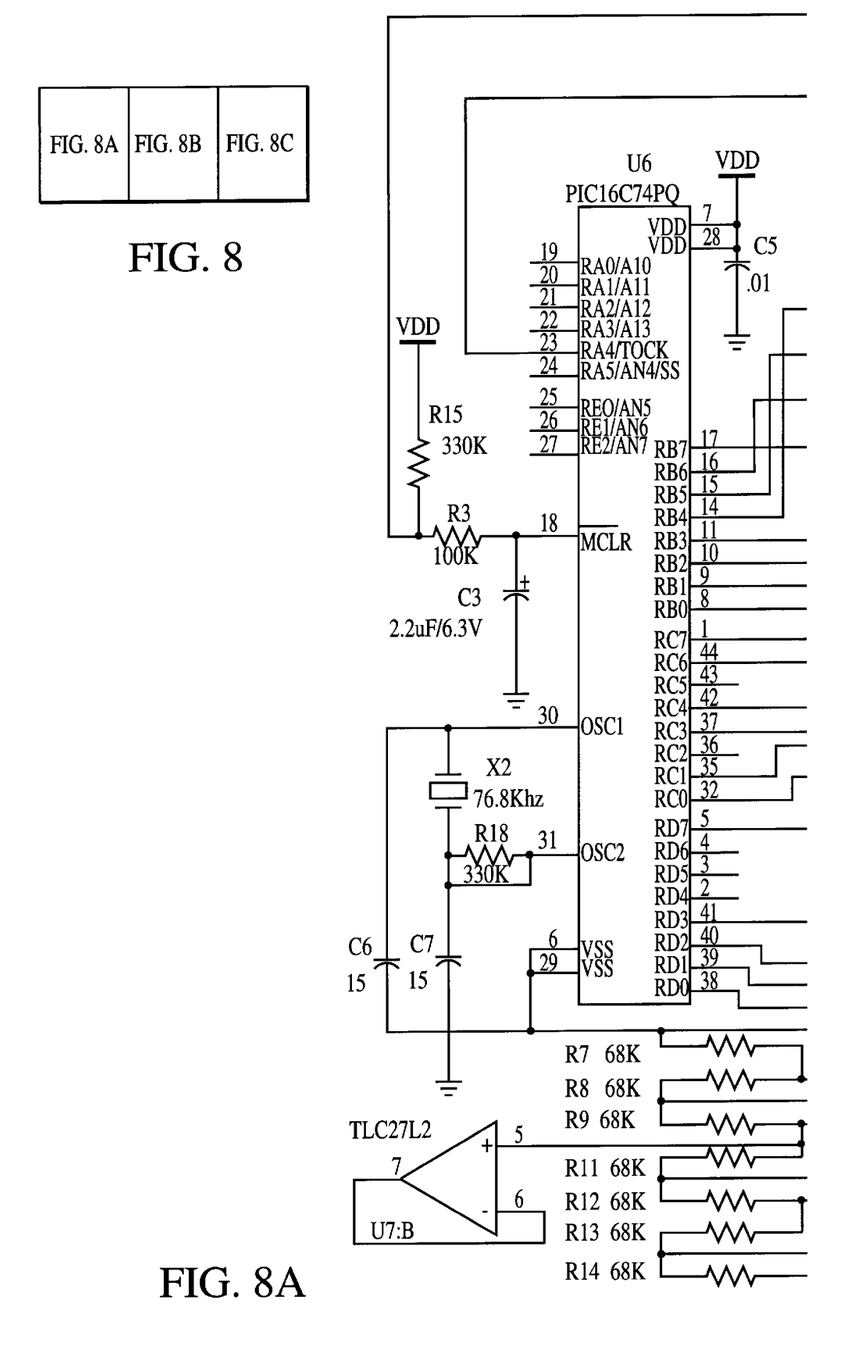
FIG. 8 is the schematic circuit diagram for the ambulatory body position monitor.
Figure 8B:
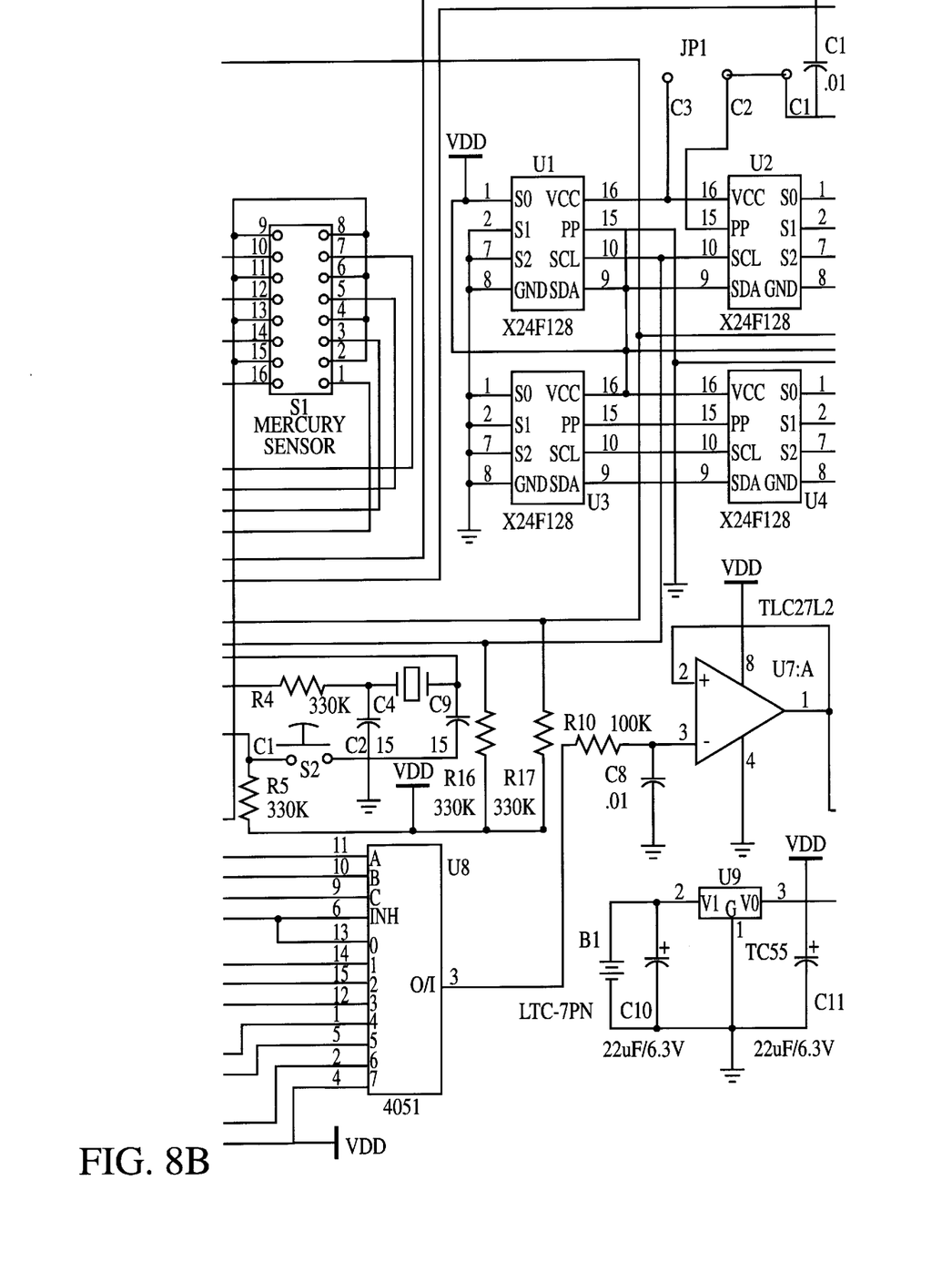
Figure 8C:
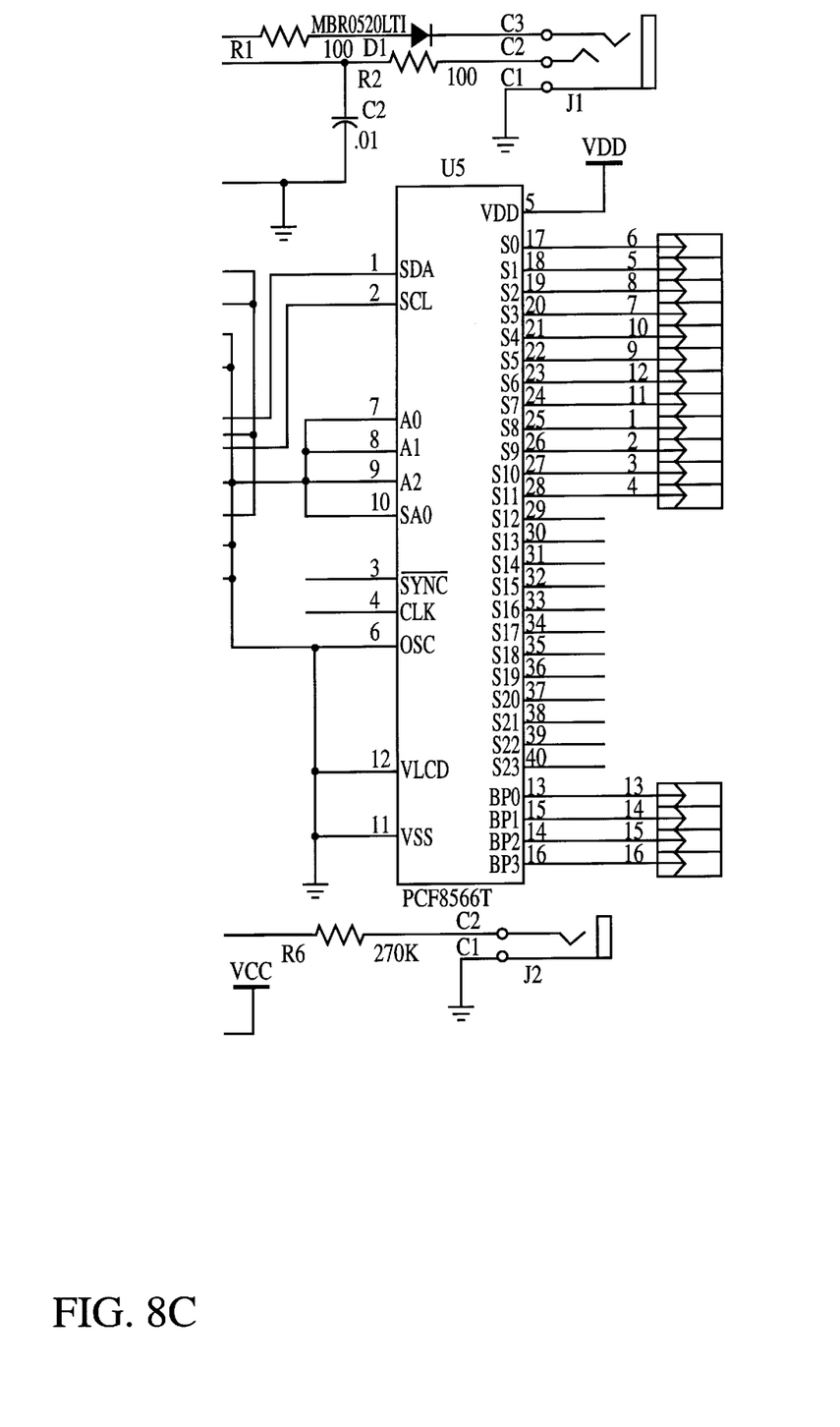

A storage device suitable for use in this embodiment has been found to be 32K of solid-state memory (four 8K×8 byte nonvolatile chips). With sampling of the sensor output every second and determining the sensor's dominant position during this period on a thirty or sixty second basis, this storage device can store such data for up to twenty-two days. A major advantage of using nonvolatile memory is that the data is always resident and retrievable, and corruption of this data is remote even if the monitor's batteries fail. A schematic circuit diagram for the ambulatory body position monitor is shown in FIG. 8.

By increasing this sampling rate to approximately 10 samples per second, it was determined that the rate of change from one position to another could also be measured.

To illustrate the operation of the above described hardware, consider the situation where the application program for the microprocessor was written to yield the following mode of operation to study patients with sleep disorders: All eight active sensor elements, as an eight bit byte (group), are sampled once per second. Each byte sample is then checked against a decoding table (i.e., truth table with 256 combinations) to determine which one of the six defined body positions (i.e., patient lying supine, prone, or on right or left side, sitting, walking) is indicated by the sensor's output. If the sensor's output matches any of the six identified table groups, a count representing an identified body position is entered into the corresponding bin of a 6-bin histogram. After monitoring such positional data for a chosen time epoch, the bin having the largest numbers of counts is indicative of the dominant body position which existed at the sensor during the time epoch in question. This position data is then saved in memory for each time epoch which passes during this positional monitoring process.

In addition to identifying basic body positions by mercury settling to the bottom-most position of the sensor relative to gravity and contacting at least one or as many as four electrode posts of the eight active posts at any one time, the occurrence of the mercury splashing across the electrodes as the result of sensor's motion provides information regarding the amount and intensity of this motion. During natural body movements, such as changing sleeping positions, rolling or twisting about, etc., splashing of the mercury occurs which provides a means for quantifying the amount and intensity of this motion.

Using software detection and filtering algorithms, the microprocessor's firmware provides a measure of the number of times the mercury splashes across the active electrode posts. This information provides a quantifiable measure of the body movement associated with this degree of mercury splashing.

Therefore, besides the determination of the predominate body position, movement activity while in each identified body position can be assessed as an independent measure. For this measure, the monitor is programmed to count the number of splash events or electrode hits per recording time epoch that are not related to the predominate body position as determined by the previously mentioned truth table.

Figure 6:
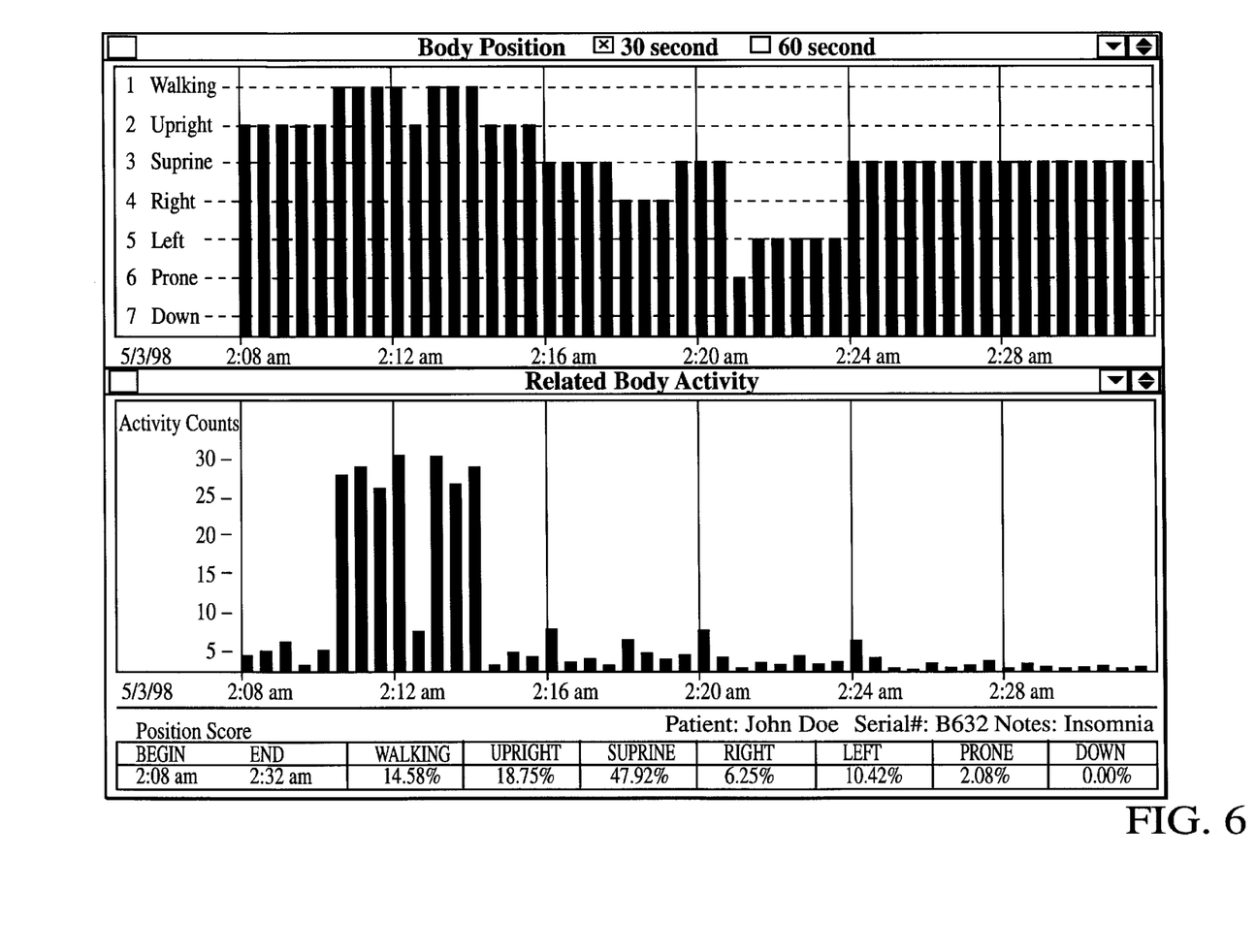
FIG. 6 displays an upper bar graph output of an ambulatory monitor worn at the chest of an insomniac patient showing the patient's dominant body position during each thirty second interval during the monitoring period. The lower bar graph shows the patient's related movement activity during this same period and shows how this information is used to distinguish walking activity from the patient generally being in an upright position. Finally, a box diagrams shown at the bottom that illustrates the percentage of time the patient was in each of these basic body positions during the monitoring period.
Figure 7:
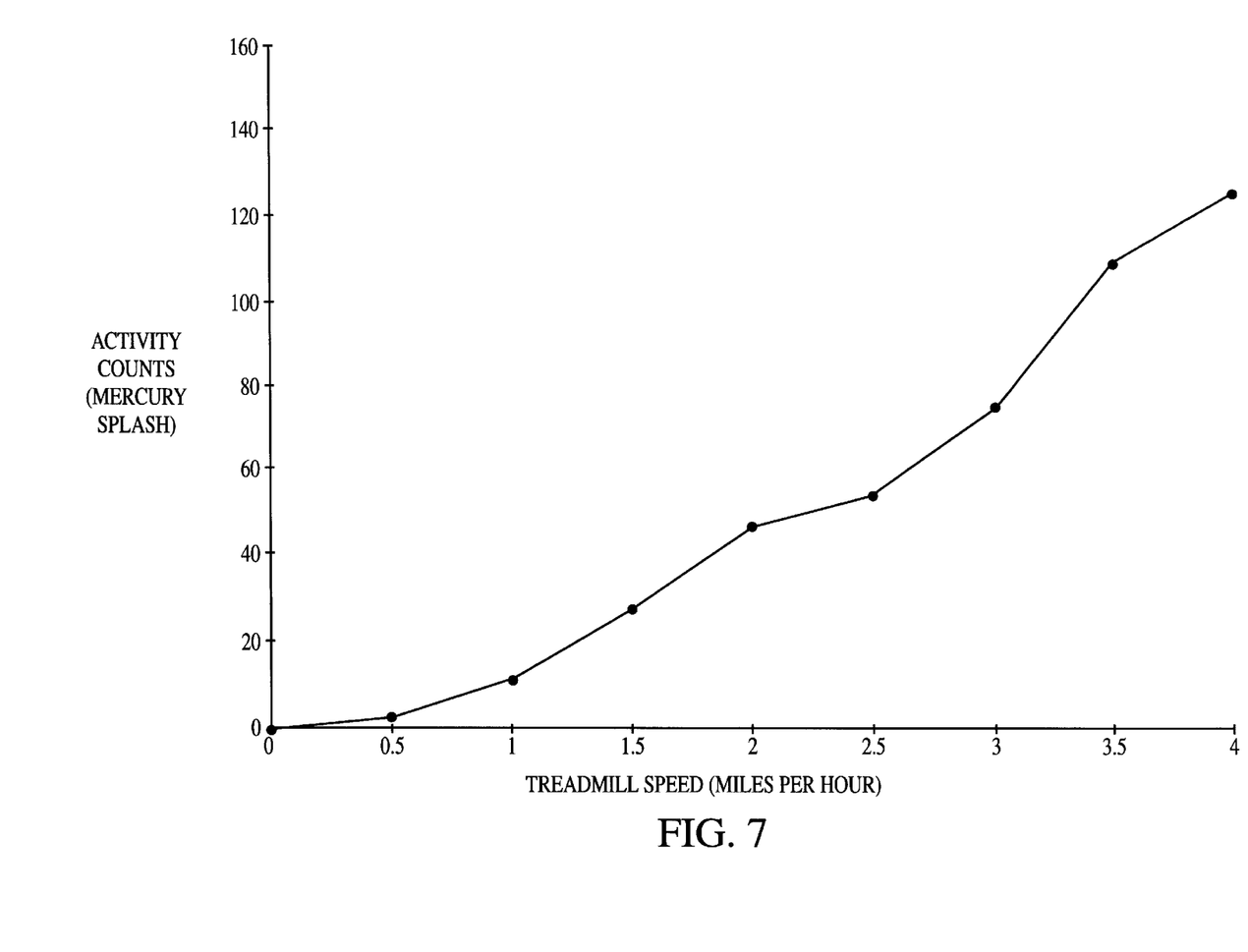
FIG. 7 shows the generally linear relationship of activity counts generated by mercury splashing within a sensor worn by one who walks on a treadmill at increasing rates of speed from zero to four miles per hour.

Also, when the body is determined to be in the upright or standing position, excessive splashes indicate walking activity, while little or no splash activity indicates a more stationary or standing position. As shown in FIG. 7, activity data generated by subjects walking on a treadmill with the monitor attached to their chest is essentially linearly related to the indicated speed of the treadmill from zero to four miles per hour. This activity data is also saved in memory for each time epoch during the monitoring process. An example of this data is shown in FIG. 6.

An interface device suitable for use in the embodiment shown in FIG. 2 serves two important functions: controlling duplex serial data flow between the monitor and an external computer, and providing precise time synchronization in those situations when more than one monitor are in operation. To accomplish these functions a smart cable was developed that allows for direct duplex communication between the monitor and an external computer. This is accomplished by using an embedded circuit in the cable to convert serial input/output monitor data to RS232 format for compatibility with the external computer. This cable allows each monitor to be preset to start recording at the same time of day and allows each to be synchronized with the clock of the external computer.

With such interfacing capabilities, an external computer can be programmed to provide the functionality to: (1) read and clear the monitor's memory, while setting the intermediate-recording interval, (2) save and recall position and activity data from a hard drive or floppy disk, (3) set monitor recording delays (used to synchronize monitors), and (4) display and print data.

Figure 4:
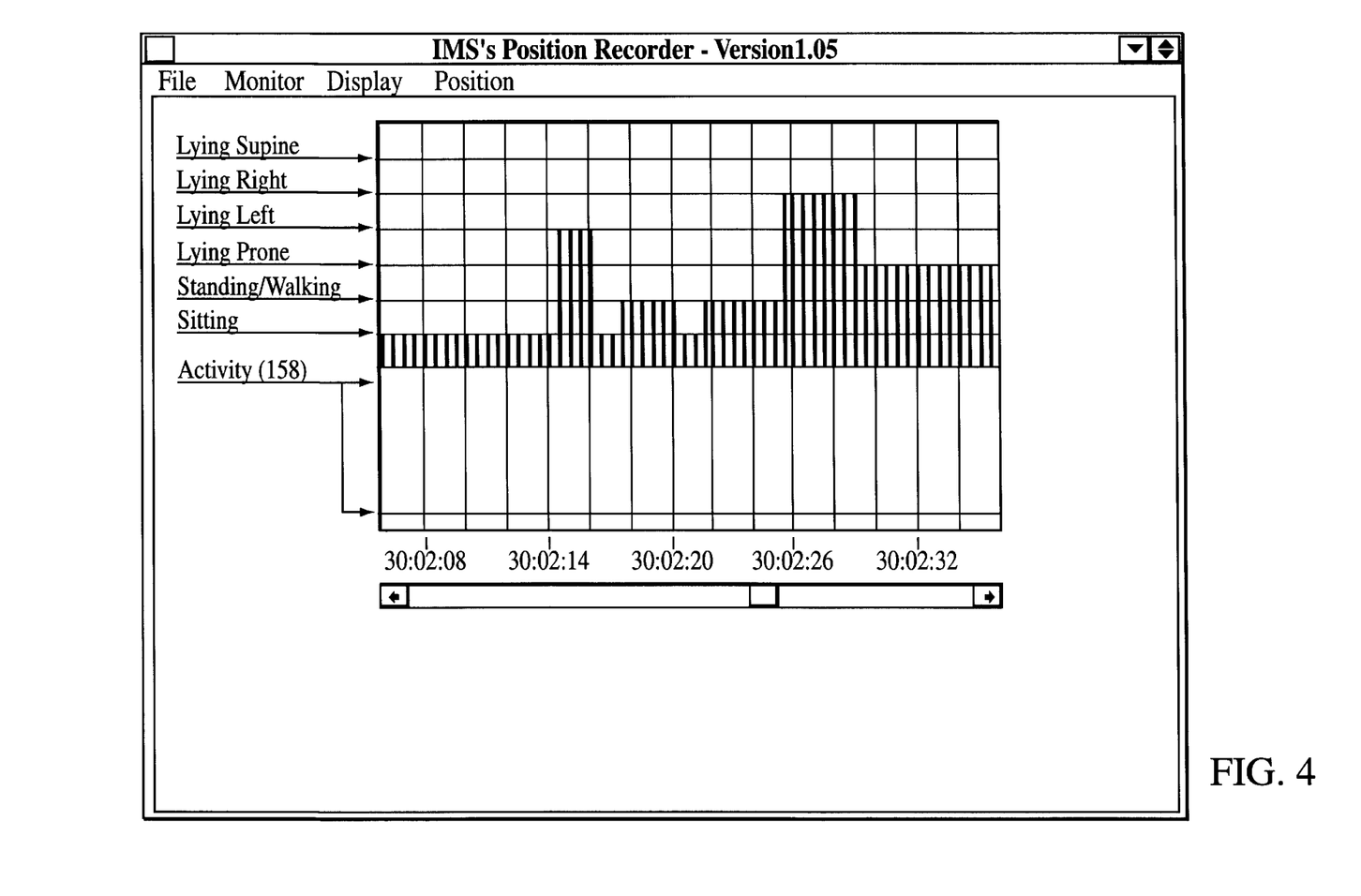
FIG. 4 is the bar graph output of ambulatory body position monitors worn at the chest and thigh of a sleeping walking patient showing an actual sleepwalking event lasting approximately six minutes.

When the monitor's data is downloaded to an external computer, the data may be analyzed in a number of ways. For example, the data can be both converted to an ASCII text file for spread sheet compatibility and displayed on a personal computer screen in bar graph form for ease of viewing. An example of this format is shown in FIG. 4 for the monitoring of a patient with a sleepwalking disorder and in FIG. 6 for the monitoring of a patient with insomnia.

Depending on the purpose of the monitoring activity, it may be appropriate to locate the monitor on any one of a number of measurement sites on the body of the subject to-be-monitored. For example, for sleep disorder studies, measurement sites at the chest (center line of the thorax), thigh (above the knee) and ankle have been found to be useful. Depending on the location of the monitor, a truth table for that body position can be developed to decode the sensor's output to distinguish the defined body positions of interest.

Figure 5:
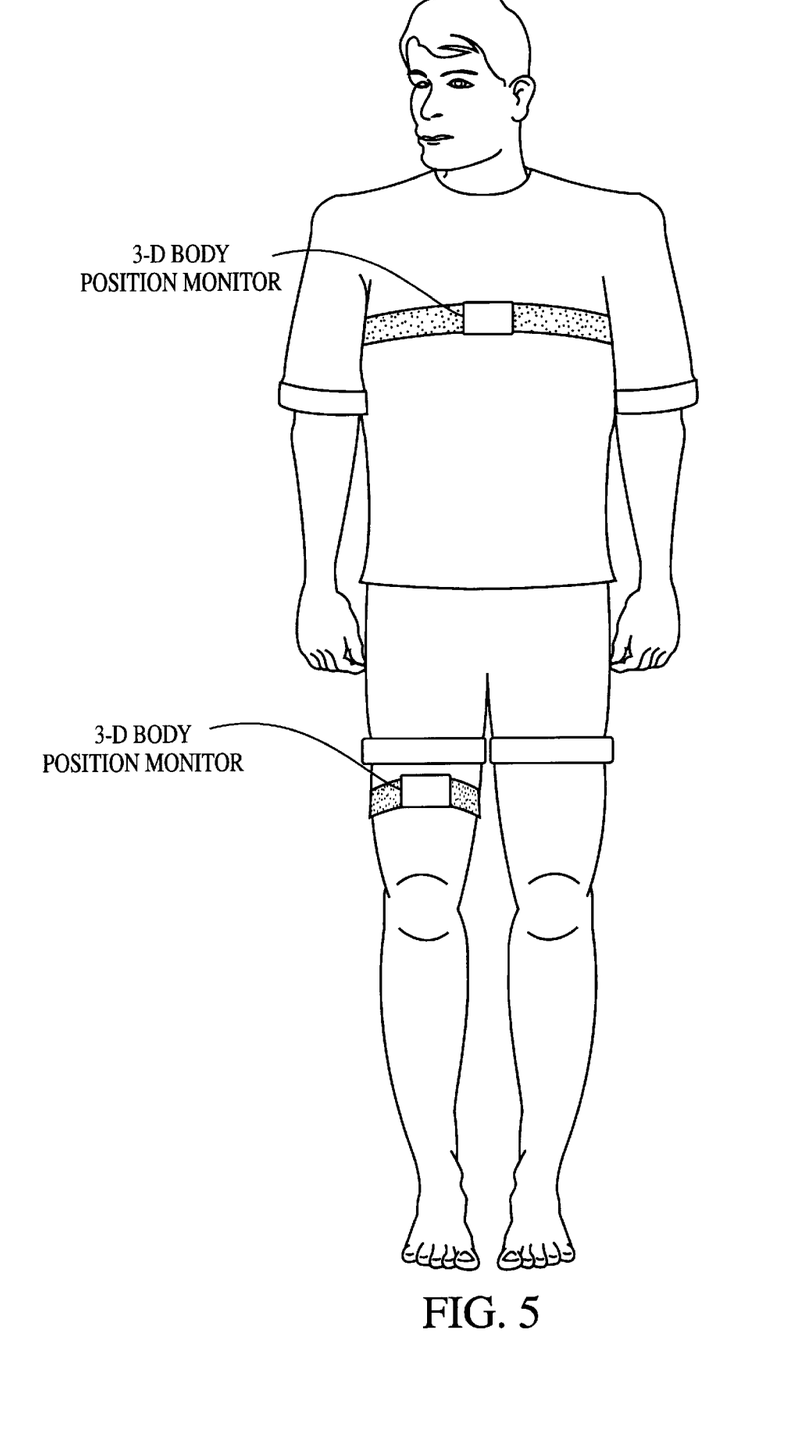
FIG. 5 depicts various measurement sites where ambulatory body position monitors might be mounted to distinguish between defined body positions of interest.

For some body positions, it may be necessary to use more than one monitor and to simultaneously analyze the monitor's outputs in order to distinguish such positions. For example, if in sleep disorder studies the distinction between sitting and walking or standing is not important, then a single monitor at the chest will suffice. If however, the sitting and standing/walking positions need to be separately identified, then a second monitor on the thigh or ankle is required in addition to the monitor on the chest. Such monitor arrangements are shown in FIG. 5.

For the purpose of monitoring the physical positions of other parts of the body, it would be appropriate to locate the monitor at other measurement sites, including the arms, legs, trunk or head of the subject to be monitored. For example, for sleep apnea studies, it would be of interest to monitor the position of the head. Similarly, for behavior assessments such as hyperactivity, the position and related motion of the subject's trunk, legs, arms and hands would be of great interest.

To determine the accuracy of an embodiment of the present invention configured for use in sleep disorder studies, sleepingwalking patients from the Johns Hopkins Sleep Disorder Center wore such monitors while in the sleep lab where their sleep was recorded on video tape. The video tape was time synchronized with the monitors' outputs which were analyzed to identify any significant events (e.g., at least five minutes of consecutive sitting up of standing up) during the patients' nights sleep. These events were then checked against the independent observations from the video tapes. All of the video taped events were detected by the monitors. One of the patients had a six minute standing and walking episode including a conversation with the research staff, with no recall of the event the next day. The monitor's output for this period was previously shown in FIG. 4.

The programmable nature of the control unit used in the ambulatory body position monitor disclosed herein, means that the present invention can have many embodiments. For example, for some applications it may prove to be beneficial to add a display unit, such as a LCD readout, for continually displaying the positional status of the monitor, as shown in FIG. 2.

In another application for the treatment of patients with sleepwalking disorders, it has been found beneficial to provide the monitor with the capability to respond to the data being collected and to sound an alarm when the user's position is measured to assume a specified position. This is easily achieved by adding an alarm unit to the monitor as shown in FIG. 2. Another variation of this embodiment would be the addition of a radio frequency transmitter to signal a remote, wireless receiver that would in-turn sound an alarm at the receiver's remote location, or would automatically dial a telephone at a second remote location to announce the existence of the alarm condition.

For other applications where it is desire to have only this alarm capability, while at the same time reducing the cost of the monitor, the alarm unit can be added and the storage and interface devices eliminated from the monitor. A suitable alarm for this application is a piezo type with a built in driver and operating at about 2,400 hertz and yielding 95 decibels. Such an alarm requires a 12 volt battery for power rather than the lithium battery which has been found to be satisfactory for powering the basic monitor shown in FIG. 2. Additionally, it may be controlled by a ultra-low power, CMOS micro controller Microchip PIC16C71 with a 1K×14 bit internal nonvolatile resident memory for the microprocessor's application program, with an on-chip, analog to digital converter and 13 input/output pins.

As an alarm monitor for sleepwalkers, it has been found that the defined body positions of interest include only the upright position and the motion of walking. The application firmware program for this monitor can be written accordingly to provide that if walking occurs for greater than a specified period (e.g., 15 or 30 seconds), the alarm unit is sounded until a reset button is pressed, as shown in FIG. 2. Additionally, this application program can provide that the micro controller only be activated when the monitor is in the upright position. This allows the power for the micro controller to be reduced to about 2 micro amps when the monitor is in the lying plane for longer than a specified period (e.g., 5 minutes). When the subject stands, the upright sensor signal powers up the monitor.

A further application of the present invention would be to integrate the positional and motion detecting properties of the device with other monitoring instruments, such as oximeters, apnea monitors, respiration monitors, airflow monitors, heart rate monitors, activity and other types of medical monitors for the purposes of gaining a better understanding of the physiological function being measured. For example, the position and motion of the subject's body, head or limbs could provide valuable qualitative information for the rejection of artifacts (e.g., false oximeter indicated periods of breathing abnormalities in sleep apnea studies) and a more accurate assessment of the physiological function being monitored.

It will be appreciated that the ambulatory body position monitor disclosed herein is seen to achieve its primary object of providing an improved position monitor having additional motion recording and alarm-sounding capabilities. Furthermore, this ambulatory monitor eliminates the requirement that such monitors be connected through cables to external data storage and processing devices, thereby often effectively dictating that such monitoring activities be conducted in clinical laboratories.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention as hereinafter set forth in the claims.

We claim:

1. An ambulatory body position monitor that is located at a measurement site on a user whose position is to be monitored, comprising:

a three-dimensional-position monitoring, mercury sensor, a programmable control unit that receives as input the output from the sensor and has the capability to sufficiently interpret said input so as to determine the position and extent of motion with respect to gravity of the measurement site at which said sensor is located on its user's body, a storage device, operable by said control unit, that stores time-stamped, data regarding the user's body position, an interface device, operable by said control unit, that has the capability of transferring said stored data to an external computer, a display unit, operable by said control unit, that visually communicates information regarding the user's body position, wherein, for monitoring subjects with sleepwalking and other sleep disorders and for which it is necessary to distinguish between the user's positions of sitting, walking or standing, a first monitor is situated on the user's chest and a second monitor is situated at a location chosen from among the group consisting of locations on the thigh and the ankle.

2. An ambulatory body position monitor as recited in claim 1, wherein:

said interface device includes a smart cable that allows for duplex communications between said monitors and an external computer that is used to synchronize and analyze the outputs of said monitors.

3. An ambulatory body position monitor as recited in claim 2, wherein:

said programmable control unit includes a microprocessor having solid-state programmable, resident memory, an analog to digital converter and a serial communication interface.

4. An ambulatory body position monitor as recited in claim 3, wherein:

said storage device includes nonvolatile, solid-state memory.

5. An ambulatory body position monitor as recited in claim 3, wherein:

said programmable control unit further includes the capability to interpret said sensor input so as to determine the extent of the user's physical motion in each body position.

6. An ambulatory body position monitor that is located at a measurement site on a user whose position is to be monitored, comprising:

a three-dimensional-position monitoring, mercury sensor, a programmable control unit that receives as input the output from the sensor and has the capability to sufficiently interpret said input so as to determine the position with respect to gravity of the measurement site at which said sensor is located on its user's body, an alarm unit with audio output device, operable by said control unit, that can generate an audible alarm signal in response to a set body position being detected by said sensor, a selection input device, connected to said control unit, for setting the desired operating parameters of said monitor, including the capability to disarm said alarm unit, and a radio frequency transmitter, connected to said control unit, for signaling a remote, wireless receiver to sound an alarm at said remote location.

7. An ambulatory body position monitor that is located at a measurement site on a user whose position is to be monitored, comprising:

a three-dimensional-position monitoring, mercury sensor, a programmable control unit that receives as input the output from the sensor and has the capability to sufficiently interpret said input so as to determine the position with respect to gravity of the measurement site at which said sensor is located on its user's body, an alarm unit with audio output device, operable by said control unit, that can generate an audible alarm signal in response to a set body position being detected by said sensor, a selection input device, connected to said control unit, for setting the desired operating parameters of said monitor, including the capability to disarm said alarm unit, and a radio frequency transmitter, connected to said control unit, for signaling a wireless receiver, that is situated at a first remote location, to dial a telephone to announce at a second remote location the alarm condition.

8. A method for monitoring and recording the position of the body of a fully ambulatory subject, comprising the steps of:

locating a three-dimensional-position monitoring, mercury sensor on a selected measurement site of the subject, generating, by using inherent contact of the mercury with electrode posts within said sensor, sensor output data that quantifies the position with respect to gravity of said measurement site, generating, by using inherent splashing of the mercury in said sensor, sensor output data that quantifies motion activity with respect to gravity of said measurement site, calibrating sensor output data so as to distinguish between and define selected positions of interest of the measurement site, sampling sensor output data at prescribed time intervals, using said sensor calibration, associating with each data sample a determination of which of the defined positions is in existence at the measurement site at the time of the data sample, sounding an audible alarm signal in response to a set body position being detected by said sensor, and using a radio frequency transmitter to signal a remote, wireless receiver so that said alarm is sounded at a remote location.

9. A method for monitoring and recording the position of the body of a fully ambulatory subject, comprising the steps of:

locating a three-dimensional-position monitoring, mercury sensor on a selected measurement site of the subject, generating, by using inherent contact of the mercury with electrode posts within said sensor, sensor output data that quantifies the position with respect to gravity of said measurement site, generating, by using inherent splashing of the mercury in said sensor, sensor output data that quantifies motion activity with respect to gravity of said measurement site, calibrating sensor output data so as to distinguish between and define selected positions of interest of the measurement site, sampling sensor output data at prescribed time intervals, using said sensor calibration, associating with each data sample a determination of which of the defined positions is in existence at the measurement site at the time of the data sample, sounding an audible alarm signal in response to a set body position being detected by said sensor, and using a radio frequency transmitter to signal a remote, wireless receiver, that is situated at a first remote location, to dial a telephone to announce at a second remote location the alarm condition.

* * * * *